United States Patent [19]
Mullerat et al.

[11] Patent Number: 6,004,587
[45] Date of Patent: *Dec. 21, 1999

[54] THERAPEUTIC, PRODUCTION AND IMMUNOSTIMULATORY USES OF BIOCIDAL COMPOSITIONS

[75] Inventors: Jaime Mullerat; David A. Hazlett, both of Raleigh, N.C.; William A. Curby, Haingham, Mass.; Peter Kilpatrick, Cary, N.C.

[73] Assignee: Bioxy Inc., Raleigh, N.C.

[*] Notice: This patent is subject to a terminal disclaimer.

[21] Appl. No.: 09/181,308

[22] Filed: Oct. 28, 1998

Related U.S. Application Data

[63] Continuation of application No. 08/363,176, Dec. 23, 1994, Pat. No. 5,830,511, and a continuation-in-part of application No. 08/260,624, Jun. 16, 1994, abandoned, which is a continuation-in-part of application No. 07/904,160, Jun. 25, 1992, abandoned.

[51] Int. Cl.$^6$ .......................... A61K 33/14; A61K 33/20; A61K 33/00
[52] U.S. Cl. .......................... 424/661; 424/662; 424/663; 424/665; 424/723
[58] Field of Search ..................... 424/661, 662, 424/663, 665, 723

[56] References Cited

U.S. PATENT DOCUMENTS

| | | | |
|---|---|---|---|
| 3,585,147 | 6/1971 | Gordon | 424/661 |
| 4,296,103 | 10/1981 | Laso | 424/130 |
| 4,507,285 | 3/1985 | Kuhne | 424/130 |
| 4,880,638 | 11/1989 | Gordon | 424/662 |
| 5,830,511 | 11/1998 | Mullerat et al. | 424/661 |

*Primary Examiner*—Deborah C. Lambkin
*Attorney, Agent, or Firm*—White & Case LLP

[57] ABSTRACT

The invention relates to methods employing pH-buffered, redox-stabilized compositions comprising halide and oxyhalide ions. The compositions can be administered to food animals to effect enhanced food utilization, lower mortality, decreased nitrogen excretion, decreased dependence on antibiotics and vaccines, overall enhanced health and immunostimulation in the animals. Additionally, the compositions can be used to treat food animal carcasses to reduce food-borne pathogens and spoilage organisms.

8 Claims, 2 Drawing Sheets

THERAPEUTIC, PRODUCTION AND IMMUNOSTIMULATORY USES OF BIOCIDAL COMPOSITIONS

This application is a continuation of application Ser. No. 08/363,176, filed Dec. 23, 1994 which issued as U.S. Pat. No. 5,830,511 on Nov. 3, 1998 and is a continuation-in-part of application Ser. No. 08/260,624, filed Jun. 16, 1994, abandoned, which is a continuation of application Ser. No. 07/904,160, filed Jun. 25, 1992, abandoned.

BACKGROUND OF THE INVENTION

This application relates to methods employing compositions having selective biocidal, therapeutic, production and immunostimulatory action, based on concentration and exposure time, against living cells and microorganisms including Gram negative and Gram positive bacteria and other pathogens. The invention relates to the treatment of animals infected with such pathogens, as well as to treatment of noninfected animals, by administration of pH-buffered, redox-stabilized compositions comprising halide and oxyhalide ions to the animals. The free radical oxyhalide intermediates formed by the compositions produce immunostimulatory effects in the animals and result in increased food utilization, lower mortality, decreased nitrogen excretion and overall enhanced health of animals, as well as microbial reduction in foods. Moreover, because of their efficacy as therapeutic and immunostimulatory agents, the administration of said compositions to food animals results in decreased dependence on vaccines and anti-biotics.

It has long been known that various chlorine-containing compounds can be used as biocidal agents. The literature contains many references to chlorine gas, various chlorites and chlorine dioxide as materials that can be used to kill microorganisms. Many patents teach that chlorine dioxide is an effective microbicide and also that it is a powerful and effective oxidizing agent useful in killing various microorganisms. Thus, there is a wide variety of patents and prior art references which describe the production of chlorine dioxide and/or the use of stabilized chlorine dioxide solutions.

The prior art describes many processes for the direct use of chlorine dioxide as a biocide. The prior art also describes many processes for the production of stabilized chlorine dioxide by the addition of a variety of inorganic compounds such as inorganic boron and/or various peroxides, including hydrogen peroxide (see, for example, Laso, U.S. Pat. No. 4,296,103; Kuhne, U.S. Pat. No. 4,507,285; and Gordon, U.S. Pat. No. 4,880,638).

Chlorine dioxide, however, also has many shortcomings. For example, it is a potentially hazardous material which is generally difficult to produce and apply where needed. Chlorine dioxide is also corrosive, and its formation requires considerable amounts of acid which add to its corrosive properties.

Gordon, U.S. Pat. No. 4,880,638 discloses an improvement in the previously known chlorine-based biocidal compositions. The Gordon compositions do not produce measurable amounts of chlorine dioxide, but do generate interactive intermediates, including but not limited to oxyhalogen reactants, which serve to provide the compositions with microbicidal properties. Gordon discloses the utility of the compositions as surface disinfectants.

Other publications have provided further insight into the chemistry of oxychloro compositions and have disclosed their biocidal properties (see, for example, Ullmann, et al., Infection 12, 225–228 (1984); Kühne, European Patent No. EP0093875; and Gordon, et al., Environ. Sci. Technol. 25, 468–474 (1991)).

The food animal industry loses substantial amounts of money yearly due to infection of the animals resulting in attenuation of growth, loss of animal size, and death of animals. Losses further occur due to the contamination of animal carcasses on the market shelf by foodborne pathogens and spoilage organisms.

In view of the foregoing, it is apparent that it is desirable to have a therapeutic, production, and immunostimulatory drug for use in the food animal industry that is benign to the host animals, less expensive and as effective as other immunostimulatory drugs, such as corticosteroids, which can have undesirable side effects. Furthermore, it is desirable to have such a composition which is useful as a disinfectant for the food industry.

SUMMARY OF THE INVENTION

It is an object of this invention to provide a composition that is safe and economical to use as a therapeutic, production and immunostimulatory drug; has outstanding cellular disinfection action; and can be administered to food animals in order to (1) stimulate the immune system, (2) increase food utilization (as reflected by decreased nitrogen excretion and reduced feed intake per kg of weight gain), (3) reduce mortality in microorganism-infected food animals, (4) decrease dependence of animals on vaccines and antibiotics, and (5) enhance overall health and vitality of animals.

It is a further object of the invention to provide a method for reducing foodborne pathogens and spoilage organisms in food animal carcasses.

The compositions set forth in detail in this disclosure represent redox-buffered stoichiometric solutions which contain little or no chlorine dioxide or so-called "stabilized" chlorine dioxide prior to triggering which may ensue in situ. Highly sensitive analytical measurements have been used which would detect as low as 1 ppm (parts per million) of chlorine dioxide or chlorine-dioxide-containing complexes in the solutions of this invention, and no chlorine dioxide was detected. The active ingredients produced by the compositions described here are halogen-oxyhalogen, redox-buffered intermediates which do not generate chlorine dioxide. These intermediates are not only effective biocides but are also apparently immunostimulatory and, in the instant disclosure, are shown to enhance the vitality and increase the food utilization of food animals, as well as to reduce mortality in microorganism-infected food animals, when administered to the animals. This activity is achieved without the necessity of producing chlorine dioxide per se. However, the interaction of the compositions in vivo or in vitro can result in the production of chlorine dioxide under specific conditions.

The microbicidal efficacy of the stabilized compositions has been extensively tested, as has its efficacy as a therapeutic, production and immunostimulatory drug. The compositions utilized in this invention have been tested as enhancers of food utilization and as reducers of mortality (1) in chicks infected with S. typhimurium, (2) in poultry infected with Bordetella avium, (3) in poultry with "spiking mortality disease," caused by viral infection, (4) poultry infected with gumboro virus, (5) under market conditions with healthy swine, and (6) under market conditions with healthy broiler chickens.

The compositions have further been tested and found effective in reducing foodborne pathogens and spoilage organisms in food animal carcasses.

DETAILED DESCRIPTION OF THE INVENTION

Figure 1:
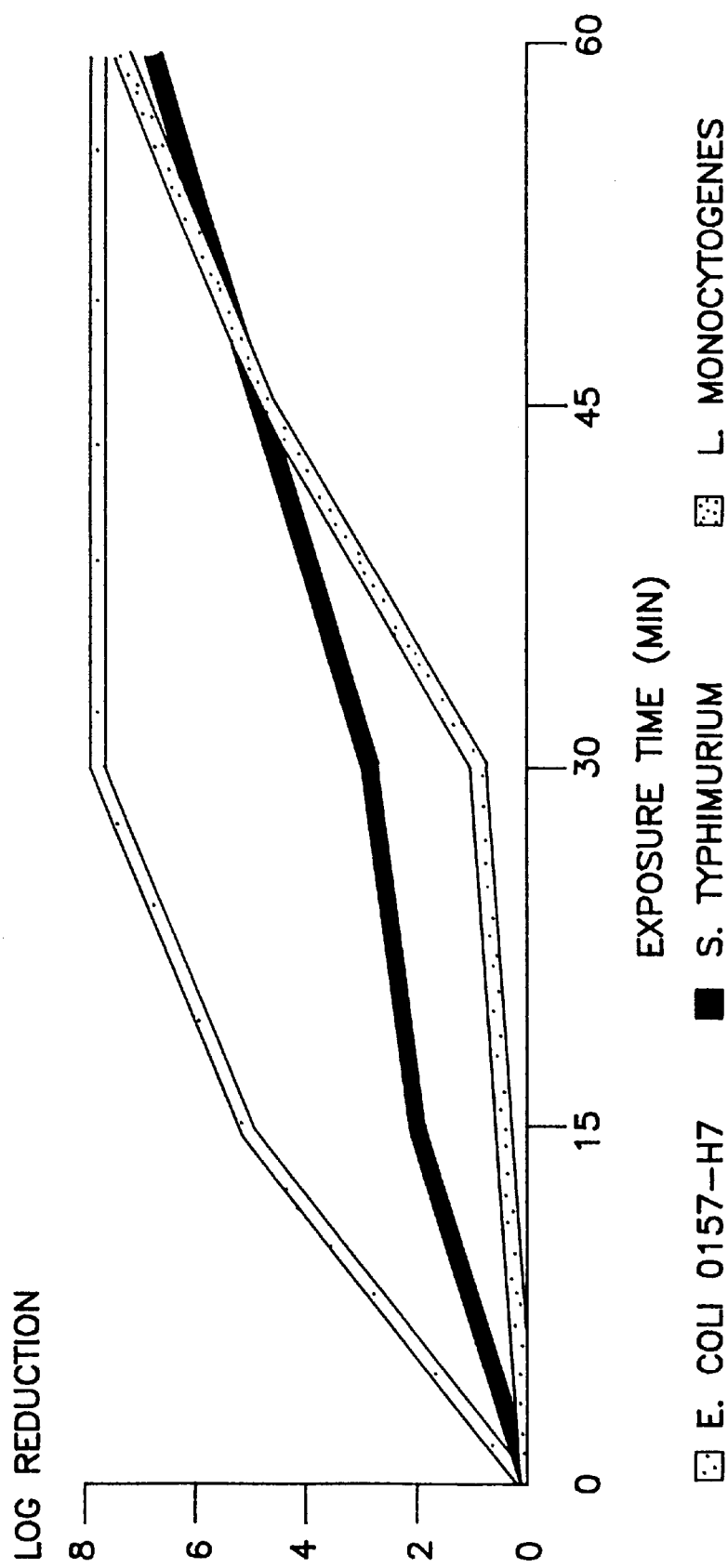
FIG. 1 shows the effect of the composition of Example 1 on the growth of three bacterial strains.

The instant invention relates to specific uses of halide-oxyhalide compositions. Specifically, a halide-oxyhalide composition at various dilutions has been determined to (1) stimulate the immune system, (2) increase food utilization of food animals (as reflected by decreased nitrogen excretion and reduced feed intake per kg weight gain), (3) reduce the mortality of microorganism-infected food animals, (4) decrease dependence of animals on vaccines and antibiotics, and (5) enhance the overall health and vitality of said food animals.

The instant invention further relates to uses of the compositions in the disinfection of food animal carcasses. The compositions have been determined to be effective in this regard.

According to one embodiment of the invention, the compositions are formed upon mixing water with a source of chlorite ions, a source of chloride ions and a source of chlorate ions. These compositions have a molar ratio of chlorite ions to chlorate ions in the range from 2:1 to about 1000:1, a molar ratio of chlorite ions to chloride ions in the range from 0.1:1 to about 1000:1 and a molar ratio of chloride ions to chlorate ions in the range from 0.1:1 to about 1000:1. The chlorite ion source is present in amounts from about 400 grams to about 0.04 milligrams per thousand grams of water.

The composition can be administered to infected animals to kill microorganisms which have a high infectivity and, accordingly, reduce mortality. The composition can be administered to healthy hosts to enhance feed utilization and overall vitality. The composition can also be employed in the treatment of food animal carcasses to reduce foodborne pathogens and spoilage organisms.

In preparing the composition described herein, various commercially available materials are utilized as the starting materials. For example, the source of chlorite ions can include materials such as alkali metal chlorites and related compounds. Sodium chlorite is especially useful in preparing the compositions of this invention because of its availability and its solubility in water. Other suitable sources for the chlorite ions include the alkaline earth metal chlorites, as well as ammonium chlorite.

Suitable sources of chlorate ions include various commercially available chlorates with alkali metal chlorates being preferred. It has been found that sodium chlorate and potassium chlorate are especially useful in producing the compositions of this invention because of their solubility and availability. Other sources of the chlorate ions include the alkaline earth metal chlorates and ammonium chlorate.

Suitable sources of chloride ions include various commercially available chlorides, with alkali metal chlorides being preferred. Sodium chloride and potassium chloride are especially useful because of their cost and solubility. Alkaline earth metal chlorides and ammonium chlorides can also be used.

In preparing the compositions, sufficient water should be available to dissolve the starting materials. While water is an essential ingredient, it should be understood that other solvents can also be present such as various alcohols, glycols and related solvents. It has been found that water should be present in an amount of at least 0.1 moles per liter. The stability of the compositions can be improved by adding appropriate pH-adjusting materials to adjust the resulting composition to a buffered pH range from about 7.5 to 13.

In order for the compositions to have good biocidal, therapeutic, production and immunostimulatory properties, the concentration of the administered chlorite ion source should be sufficient to provide a range of chlorite ion concentration from 0.01 mM to 1.0 M.

A preferred molar ratio of chlorite ion material to chlorate ion material that is added to the water-containing solvent is in the range from 3:1 to 500:1 and that of chlorite ions to chloride ions is in the range from 1:1 to 50:1.

A still more preferred embodiment of the invention employs compositions wherein the molar ratio of chlorite ion to chlorate ion is in the range from 3:1 to 16:1; the molar ratio of chlorite ion to chloride ion is in the range from 0.8:1 to 5:1; and the molar ratio of chloride ion to chlorate ion is in the range from 4:1 to 16:1.

The best embodiment of the invention known to the inventors at this time employs compositions wherein the molar ratio of chlorite ion to chlorate ion is 11.8:1; the molar ratio of chlorite ion to chloride ion is 1.12:1; and the molar ratio of chloride ion to chlorate ion is 10.5:1.

The stability of the compositions can be improved by adding a pH-adjusting material to adjust the pH of the resulting mixture to a final range of 7.5 to 13. It has been found that if the pH is adjusted to about 13, the compositions are very stable and will retain their biocidal properties over long periods of storage. The concentration of the buffer can range from 0.001 M up to the saturation level of the solution. The preferred buffering materials contain phosphate salts. The preferred buffer concentration is in the range of 0.001 M to 0.5 M.

It has been found that various other materials can be added to the compositions to improve their efficacy. For example, it has been found that the addition of materials such as hydrogen peroxide will inhibit the production of chlorine dioxide. Materials such as borates, perborates, percarbonates and sulfates can also be utilized to retard the formation of chlorine dioxide. Such materials include borax, and various peroxides such as peroxysulfate, peroxyborate and peroxydisulfate.

It should be noted that the scope of the invention is not confined solely to the utilization of compositions comprising chloride, chlorite and chlorate ions. Other compositions intended for use according to the invention are comprised of other halide and pseudohalide (e.g. thiocyanate) components and provide effective alternatives to oxychlorine chemistry.

For example, it is anticipated that compositions of matter comprising bromide, bromite and bromate ions will exhibit the same utility as that described for oxychloro compositions. In fact, it would be expected that the minimal concentrations of the ion sources required for effective microbicidal activity of an oxybromine composition would be lower than for an oxychlorine formulation (Babior, B. M., in *The Biology and Chemistry of Active Oxygen,* Bannister and Bannister, Eds., Elsevier, pp. 190–206 (1984)).

Similar compositions can be formulated with iodide, iodite and iodate; fluoride, fluorite and fluorate; or with the three valence states of the pseudohalide thiocyanate. It is further anticipated that combinations of mixed oxyhalogens, for example, combinations of chloride, bromite and bromate or chloride, chlorite and bromate, will also be effective.

Although it is not intended that the inventive compositions be limited to any particular theory of operation or mechanism, it is believed that the biocidal compositions formed by mixing the aforementioned ingredients contain some type of reaction products or intermediate products that are highly effective in killing various types of virulent organisms. As will be appreciated by those skilled in the art, such intermediate products can be induced to produce final reaction products in accordance with the principle of Le Chatelier. In this instance, it is possible that the various materials that are combined can be induced to produce final reaction products that include significant amounts of chlorine dioxide. However, it has been found that if one controls and limits the amount of chlorine dioxide that is actually formed (for example, by the addition of hydrogen peroxide to the composition), the resultant intermediate products are indeed more effective than chlorine dioxide itself in killing organisms that are aggressively growing.

More specifically, it is believed that the claimed utility of the described compositions derives from their ability to form oxidative killing agents including but not limited to superoxide ions, hydroxyl radicals and hypochlorite ions. Production of these agents mimics the "respiratory burst" which occurs during phagocytic killing of invasive organisms, one of the first lines of defense in the immune system.

While some of these oxy-chlorine intermediates have been shown to possess bactericidal properties, they have also been shown to specifically possess immune system enhancing properties. Toxicological and pathological laboratory observations indicate that the intermediate products of the composition, such as dichlorine oxide, dichlorodioxygen, or tetrachlorodecaoxygen (TCDO) benefit the immune system by stimulating the production of the bone marrow, evidenced by the pronounced increase in mature granulocytes, pronormo- and normoblasts, or increased cell proliferation rate, determined by means of the BrdUrd method. Stimulation of the bone marrow leads in turn to increased numbers of leucocytes and monocytes in the peripheral blood.

In addition, the intermediate products of the compositions induce the production of large granular lymphocytes (LGLs), referred to as natural killer cells (NK-cells). These intermediates have also been shown to have effective modulator properties in the entire immune system. It is these oxychlorine intermediates which likely confer the composition its unique ability to enable food animals, such as chickens, turkeys, and pigs, to fight off possible lethal infections, such as salmonellosis and bordetellosis.

Another factor in the success of the compositions may lie in their ability to purify and disinfect the drinking water itself, thus reducing the exposure of the food animals to bacterial and virucidal pathogens.

The above mentioned agents are formed in amounts which would have no significant effect on the host, but would have a profound effect on invading pathogens, particularly since the pathogens do not inherently have the biochemical wherewithal to overcome the barrage of oxidative intermediates. The oxidative killing agents would be expected to exert their effect by such mechanisms, among others, as lipid peroxidation in the pathogens' cell membranes and halogenation of cell-wall proteins.

Once the compositions have been formulated, they can be administered for applications including but not limited to (1) the prevention and/or treatment of microorganism infection of animals, (2) as enhancers of feed utilization, (3) as enhancers of overall vitality in healthy food animals and (4) for administration onto food animal carcasses for the purpose of reducing foodborne pathogens and spoilage organisms.

In order to demonstrate the biocidal, therapeutic, production and immunostimulatory properties of the compositions, the following examples are offered. It should be appreciated that these are merely examples to show the utility and effectiveness of the compositions. The inclusion of these examples should not be interpreted in any manner as limiting the scope of the present invention to the conditions set forth in the examples with regard to the proportions as well as final concentrations and quantities of the ingredients. Similarly, the disclosure of these examples should not be interpreted in any manner as limiting the scope of the compositions solely to those containing chlorine and oxychlorine species.

EXAMPLE 1

A composition with biocidal, therapeutic, production and immunostimulating properties was prepared by dissolving 42.4 kg of sodium chlorite (80%) in 160 liters of deionized water. The mixture was stirred well until all of the solids dissolved. 3.3 kg of sodium chlorate and 19.5 kg of sodium chloride were then added to the aqueous mixture and it was stirred for approximately 10 minutes until all of the solids had dissolved. 1.4 kg of sodium borate and 1.4 kg of sodium sulfate were then added to the mixture and it was stirred for approximately 10 minutes until all of the solids had dissolved. 1.0 kg of hydrogen peroxide (35%) was added and the mixture was stirred for approximately 5 minutes. Finally a pH modifier in the form of monopotassium dihydrogen phosphate was added to the mixture and it was stirred for approximately 10 minutes until all of the solids were dissolved. The composition was filtered to remove trace impurities.

The composition resulting from the above steps had a specific gravity of 1.23. The chlorite ion was present in an amount of 2.00 moles per liter. The chlorate ion was present in the amount of 0.17 moles per liter, and chloride ion was present in an amount of 1.78 moles per liter. In all of the following examples, the tests were carried out with the composition of Example 1 diluted as specified in each Example. The concentrations set forth in the following examples refer to the final concentrations of chlorite ion.

The following in vitro and in vivo microbiological studies were performed to demonstrate the biocidal, therapeutic, production and immunostimulatory efficacy of the oxyhalogen, non-chlorine-dioxide-generating intermediates.

EXAMPLE 2

The composition of Example 1 was diluted to a concentration of 0.093 molar. Using standard AOAC microbiological testing procedures, it was added for 60 minutes to log-phase cultures of the following Gram negative and Gram positive bacteria ($10^8$ CFU*/ml). Log-phase cultures were employed as well in all the following Examples which concern the bactericidal effect of the composition.

| Gram negative bacteria: | |
| --- | --- |
| Salmonella typhimurium | NAR |
| Escherichia coli | 0157.H7 2018 |
| Gram positive bacteria: | |
| Listeria monocytogenes | ATTC 19111 |

*colony forming units

The biocidal activity was monitored at 15-minute intervals. FIG. 1 shows that each of the Gram negative and Gram positive bacterial strains has a unique biocidal sensitivity to the compound based on exposure time.

EXAMPLE 3

The composition of Example 1 was diluted to a concentration of 0.092 molar with respect to chlorite ions. Using standard AOAC microbiological testing procedures, it was added for 60 minutes to cultures of the following Gram negative and Gram positive bacteria ($10^8$ CFU/ml).

| Gram negative bacteria: | |
| --- | --- |
| *Salmonella typhimurium* | NAR |
| *Salmonella choleraesuis* | ATTC 10708 |
| *Pseudomonas aeruginosa* | ATTC 15442 |

| Gram positive bacteria: | |
| --- | --- |
| *Listeria monocytogenes* | ATTC 19111 |
| *Staphylococcus epidermidis* | ATTC 12228 |
| *Staphylococcus aureus* | ATTC 12600 |

Figure 2:
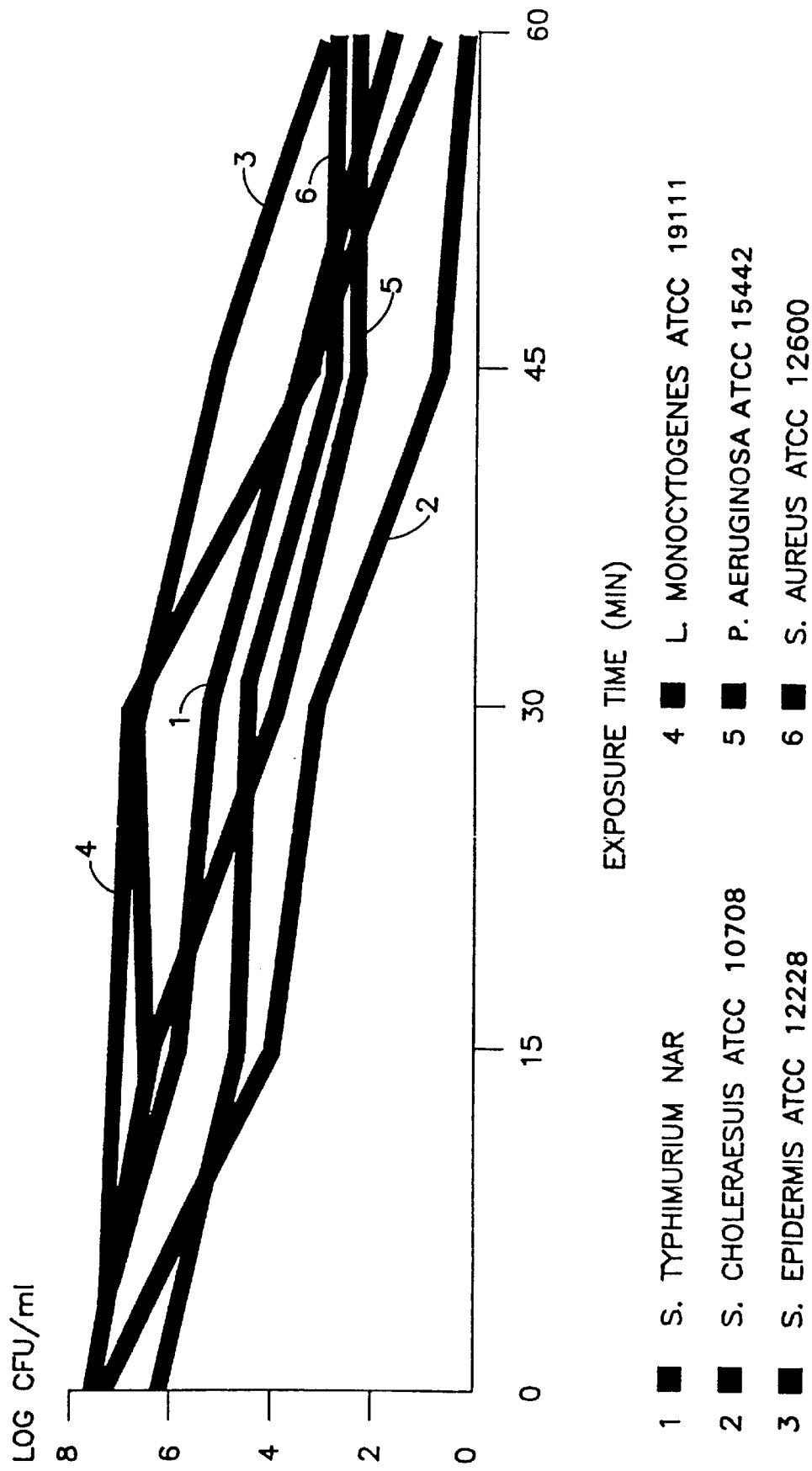
FIG. 2 shows the effect of the composition of Example 1 on the growth of six selected bacterial strains.

The biocidal activity was monitored at 15-minute intervals. FIG. 2 also shows that each of the bacterial strains has a unique biocidal sensitivity to the composition based on exposure time.

EXAMPLE 4

The objective of this study was to evaluate the biocidal efficacy of the composition in the presence of organic medium. The composition was diluted to a concentration of 0.092 molar and was added for 60 minutes to cultures, using standard AOAC microbiological testing procedures, of the highly infective strain *Salmonella typhimurium* NAR in brain-heart infusion (BHI) broth ($10^7$ CFU/ml). The biocidal activity was monitored at 15-minute intervals.

Table I shows that the composition has biocidal activity against the tested bacterial strain in the presence or absence of organic medium. Furthermore, most of the biocidal activity (2.77 logs or $\geq$99.5% reduction in BHI broth) occurs during the first 15 minutes of exposure. These results are significant because while the biocidal activity of the composition in this study was somewhat attenuated in organic medium, greater than 99.5% reduction of the bacteria within 15 minutes was nonetheless observed. The attenuation observed in this study was considerably less than what is typically seen for other biocidal compositions in organic medium.

TABLE I

Effect of an Organic Medium on the Bactericidal Efficacy of the Composition
*Salmonella typhimurium* NAR over time

| TREATMENTS | Control (0 min) log (CFU/ml) | EXPOSURE TIME (min) | | | |
| --- | --- | --- | --- | --- | --- |
| | | 15 | 30 | 45 | 60 |
| | | log reduction (a) | | | |
| BHI | 7.52 (3.28 × $10^7$) | 2.77 | 1.12 | 1.44 | 1.45 |
| dd H2O | 7.74 (5.56 × $10^7$) | 7.02 | 7.74 | 7.74 | 7.74 |

(a) - Log reductions are in respect to control. Data are an average of two experiments.

EXAMPLE 5

In this study the inhibitory activity of various concentrations of the composition of Example 1 was evaluated against a population of the highly infective bacterial strain *Salmonella typhimurium* NAR inoculated onto broiler drumstick skin.

An overnight culture of *Salmonella typhimurium* NAR was transferred to fresh BHI broth and incubated at 37° C. for 1.5 h to a population density of approximately $1 \times 10^7$ CFU/ml. One hundred microliters (approximately $1 \times 10^6$ CFU) of the bacterial suspension were spread evenly onto 2-cm² pieces of fresh broiler drumstick skin. Following inoculation, the broiler skin was held at room temperature (25° C.) for 15 min to allow for adsorption and/or attachment of *S. typhimurium* NAR to the skin. The inoculated skin was transferred to a centrifuge tube containing 30 ml of the appropriate treatment concentration.

The composition was diluted to 0.027 M, 0.054 M and 0.081 M. After a 10-min exposure to the specified treatment solution under continuous agitation at 37° C., surviving *S. typhimurium* NAR organisms were recovered from the skin. A skin rinse technique was used and consisted of vortexing the skin in 10 ml 0.1% peptone water for 1 min. The rinse solution was serially diluted in 0.1% peptone water, and viable *S. typhimurium* NAR organisms were recovered by pour plating with BHI agar supplemented with 100 ppm nalidixic acid. Plates were incubated at 37° C. for 48h and colonies counted. All trials were replicated three times.

Table II shows that the biocidal potency is dependent on the composition's concentration; increasing concentrations of the composition resulted in increased inactivation of the *S. typhimurium* NAR population.

TABLE II

Effect of Concentration of the Composition on the Growth of *S. typhimurium*

| Concentration (M) | Percent Reduction |
| --- | --- |
| control (0) | 33.0 |
| 0.027 | 63.2 |
| 0.054 | 79.7 |
| 0.081 | 87.3 |

EXAMPLE 6

A microbiological study was conducted to validate further that the composition has a selective biocidal action, based on concentration and exposure time, against living cells and microorganisms including Gram negative and Gram positive bacteria and other pathogens.

The composition was diluted to a 0.092 molar concentration and was added for 60 minutes to cultures, using standard AOAC microbiological testing procedures, of the following actively growing Gram negative and Gram positive bacteria ($10^7$ CFU/ml). The biocidal activity was monitored at 30 and 60 minutes.

| Gram negative bacteria - Salmonella species: | |
| --- | --- |
| *Salmonella typhimurium* | NAR |
| *Salmonella choleraesuis* | ATTC 10708 |
| *Salmonella worthington* | 206-4 |
| Other Gram negative bacteria: | |
| *Pseudomonas aeruginosa* | ATTC 15442 |
| *Escherichia coli* | 0157.H7 2018 |

| Gram positive bacteria: | |
| --- | --- |
| *Listeria monocytogenes* | ATTC 19111 |
| *Staphylococcus epidermidis* | ATTC 12228 |
| *Staphylococcus aureus* | ATTC 12600 |
| *Lactobacillus acidophilus* | 0606 1-B (VPI) |

The average log reduction for Gram negative strains after a 30-minute exposure was found to be 4.85 (range 2.54–7.38) and for Gram positive strains, 1.05 (range 0–1.91). The average log reduction for Gram negative strains after a 60-minute exposure was found to be 6.64 (range 5.50–7.38) and for Gram positive strains, 4.94 (range 3.87–6.72). The results of this study support further the findings in Examples 2–5.

EXAMPLE 7

This study was conducted to evaluate the effect of the composition on the microbiological quality and safety of fresh whole broilers processed under current United States Department of Agriculture (USDA) procedures. The results indicate that the composition has utility as a poultry carcass disinfectant.

The study consisted of 60 untreated control carcasses and 60 treated carcasses rinsed with transfer, pre-enrichment medium and analyzed for Salmonella, total aerobic plate count (APC), total coliform, *E. coli* and Campylobacter. The treatment used consisted of a 30-second immersion in a 31 mM solution of the composition, followed by 30 seconds of dripping dry and then the application of transfer medium to the poultry carcasses using standard AOAC microbiological testing procedures. The mean control APC was 8,100 CFU per ml rinse (average $\log_{10}=3.91$), while the mean treated APC was 2,660 ($\log_{10}=3.42$), which corresponded to a 0.49 mean log reduction (67.1%) in APC. The study showed that the composition reduced Salmonella by over 1.56 logs (>97.6% reduction), *E. coli* by >0.9 logs (>89.1% reduction), and Campylobacter by more than 1.95 logs (>98.9% reduction).

EXAMPLE 8

This study was conducted to evaluate the effect of the composition on the microbiological quality and safety of fresh broilers processed under current United States Department of Agriculture (USDA) procedures. The results of this study support further the findings in Example 7.

In this study 20 carcasses were obtained (1 at a time) from the evisceration line prior to their entering the inside-outside bird washer of a poultry processing plant. Five of the carcasses served as the untreated controls. These carcasses were immersed for 5 seconds in a 5-gallon vessel to simulate subjection to the inside-outside bird washer. After an 80-second dripping period, the carcasses were immersed in another vessel containing chill water (20 ppm chlorine) for 45 minutes, in order to simulate subjection to a chilling tank.

Five carcasses were immersed for 5 seconds in a 5-gallon vessel containing 3.84 mM of the composition. After an 80-second dripping period, the carcasses were immersed in another vessel containing chill water and 0.256 mM of the composition for 45 minutes.

Five carcasses were immersed for 5 seconds in a 5-gallon vessel containing 3.84 mM of the composition. After an 80-second dripping period, the carcasses were immersed in another vessel containing chill water and 0.128 mM of the composition for 45 minutes.

Five carcasses were immersed for 5 seconds in a 5-gallon vessel containing 3.84 mM of the composition. After an 80-second dripping period, the carcasses were immersed in another vessel containing chill water and 0.096 mM of the composition for 45 minutes.

The carcasses were aseptically introduced into sterile bags and individually rinsed for 30 seconds with 200 ml of sterile transport medium, using standard AOAC microbiological testing procedures. The carcasses were then rinsed with Butterfield's broth medium for coliform and *E. coli* analysis.

The mean coliform count for control carcasses was 88,400 CFU per ml rinse (average $\log_{10}=4.95$). The mean coliform count for carcasses treated with 0.256 mM of the composition was 496 (average $\log_{10}=2.70$), corresponding to a 99.4% reduction with respect to the control. The mean coliform count for carcasses treated with 0.128 mM of the composition was 1,340 (average $\log_{10}=3.13$), corresponding to a 98.5% reduction. Finally, the mean coliform count for carcasses treated with 0.096 mM of the composition was 1,516 (average $\log_{10}=3.18$), corresponding to a 98.3% reduction.

The mean *E. coli* count for control carcasses was 55,400 CFU per ml rinse (average $\log_{10}=4.74$). The mean *E. coli* count for carcasses treated with 0.256 mM of the composition was 218 (average $\log_{10}=2.34$), corresponding to a 99.5% reduction with respect to the control. The mean *E. coli* count for carcasses treated with 0.128 mM of the composition was 614 (average $\log_{10}=2.79$), corresponding to a 98.9% reduction. Finally, the mean *E. coli* count for carcasses treated with 0.096 mM of the composition was 858 (average $\log_{10}=2.93$), corresponding to a 98.5% reduction.

This study further demonstrates that the composition is an effective disinfectant of food animal carcasses.

EXAMPLE 9

This study was conducted to evaluate the therapeutic, production and biocidal activity of the composition in young chicks (1–14 days old) infected with *Salmonella typhimurium* ($10^5$ CFU/ml). A series of concentrations of the composition was tested. The biocidal effect of the composition, as well as changes in protein absorption, growth and feed utilization of the chicks were determined upon chronic administration of the composition, for up to 14 days, in the chicks' drinking water.

The composition was seen to have a concentration-dependent biocidal activity against the tested strain. In infected chicks given the composition at 1 mM, a mean 0.89-log (87%) reduction in initial counts was seen at 7 days and a mean 1.0-log (90%) reduction at 14 days. In infected chicks given the composition at 2 mM, the initial counts were reduced by a mean of 0.50 logs (68%) at 7 days and a mean of 0.17 logs (32%) at 14 days.

Furthermore, the results show that the composition has a biocidal activity against Gram negative bacteria in young chicks based on concentration and exposure time. These observations confirm the results from Examples 2–6 which demonstrated that Gram negative bacteria have a great biocidal sensitivity to the composition.

The composition was seen to have an effect on the growth and feed utilization of the chicks. At hatching, body weights were approximately 2.8% lower in chicks designated to receive *S. typhimurium* inoculation (Table III). No significant *S. typhimurium* major effects on body weight were noted at day 7 or 14. At days 7 and 14, chicks receiving 1 mM of the composition exhibited greater body weight than either unsupplemented controls or chicks receiving 2 mM of the composition. A significant interaction of the composition with *S. typhimurium* was observed. In the presence of *S. typhimurium* inoculation, chicks that received 1 mM composition exhibited greater body weight when compared with inoculated chicks receiving tap water or 2 mM composition at days 7 or 14. A similar effect was not noted in the absence of *S. typhimurium* inoculation. At day 7, uninoculated chicks receiving 2 mM composition exhibited lower body weight when compared with chicks receiving tap water.

TABLE III

Body weights of infected and uninfected chickens as influenced by the administration of the composition.

| Salmonella challenge | Age (days) | Composition level (mM) | | |
|---|---|---|---|---|
| | | 0 | 1 | 2 |
| | | (g) | | |
| yes | 0 | 40.2 | 42.1 | 41.4 |
| | 7 | 130.1 | 147.4 | 129.3 |
| | 14 | 322.9 | 362.8 | 319.3 |
| no | 0 | 43.1 | 41.5 | 42.5 |
| | 7 | 142.5 | 138.9 | 134.6 |
| | 14 | 326.4 | 331.2 | 322.1 |

Feed conversion ratios (FCR) are depicted in Table IV. Significantly greater gains in body weight per unit of diet consumed were observed in chicks receiving the composition (2 mM and 1 mM) from days 0 to 7. No effects associated with the composition treatments were observed for 7- to 14-day feed conversion ratios. No statistically significant effects on feed conversion were attributed to *S. typhimurium* inoculation.

TABLE IV

Feed conversion ratios as influenced by the administration of the composition to infected or uninfected chicks.

| Salmonella challenge | Age (days) | Composition level (mM) | | |
|---|---|---|---|---|
| | | 0 | 1 | 2 |
| | | (g feed/g gain) | | |
| yes | 0–7 | 1.168 | 1.107 | 1.091 |
| | 7–14 | 1.465 | 1.432 | 1.462 |
| no | 0–7 | 1.147 | 1.079 | 1.088 |
| | 7–14 | 1.575 | 1.475 | 1.493 |

The composition was further seen to have an effect on nitrogen excretion and retention in the tested chicks. Protein levels in excreta were estimated by the determination of nitrogen (Kjeldahl) from a 24 h collection of each replicate at 7 and 14 days of age. For the estimation of nitrogen retention, chromic oxide (chromium sesquioxide) was incorporated (0.3%) into the diet as a reference marker.

At day 7, chicks receiving 1 mM and 2 mM of the composition had significantly lower excretal nitrogen concentrations when compared with those chickens receiving tap water. After 7 days, the excretal nitrogen levels had fallen from an initial level of 5.93% to 5.32% in chicks imbibing a 1 mM solution of the composition and to 5.19% for chicks imbibing a 2 mM solution of the composition. No significant difference between initial and 14-day excretal nitrogen levels was observed.

After 7 days, nitrogen retention levels, expressed as mg N retained per g diet, had risen from an initial level of 20.1 to 23.2 in chicks receiving 1 mM of the composition and to 23.4 in chicks receiving 2 mM of the composition. Such results in the employed test for nitrogen retention suggest that greater amounts of protein are being synthesized and retained. As with nitrogen excretion rates, the effect of the composition on nitrogen retention was age dependent; the composition enhanced nitrogen retention in 7-day- but not in 14-day-old chicks.

The studies demonstrate that protein absorption, growth, and feed utilization are improved when the compound is administered in the drinking water of chicks infected with *Salmonella typhimurium*.

EXAMPLE 10

This study was conducted to evaluate the effect of the composition on the microflora of the gastrointestinal tract. In this study, the therapeutic and biocidal activity of the composition was evaluated in chickens infected with *Salmonella typhimurium*. A series of concentrations of the composition was tested by administration of the composition in the drinking water of 45-day-old chickens.

In this study, 6-week-old male and female broilers weighing between 1.8 and 2.3 kg each were selected. Birds were tested by cloacal swabs for the presence of Salmonella, and birds testing positive for Salmonella were destroyed. The birds which tested negative were fed a standard broiler withdrawal ration ad libitum until feed was withdrawn. The day prior to processing, feed and water were withdrawn from all birds for a period of 4 to 6 hours. Following this initial withdrawal period, an intubator was used to inoculate birds with $10^5$ CFU of nalidixic-acid-resistant *S. typhimurium* in the crop. After inoculation, birds were offered water containing one of the composition concentrations for a period of 8 hours.

This study was designed to validate that the composition is a very effective therapeutic and biocidal drug, based on concentration and exposure time, against aggressively growing Gram negative bacteria which have infected chickens. Table V shows the biocidal activity of the composition in broiler ceca contaminated with Salmonella. The Table shows that the composition has a biocidal activity against the bacterial strain based on concentration. The composition has its greatest biocidal activity at a concentration of 1.33 mM to 2 mM.

From a control level of 47.5%, the administration of the composition increased the percentage of negative ceca to between 70% and 93.3%. Birds given 1.33 mM or 2 mM of the composition had the greatest percentage of negative ceca (93.3% and 90%, respectively). These data suggest that the composition has a potential as a cecal disinfectant when used just prior to processing. The data also suggest that the composition may also reduce carcass contamination.

Examples 9 and 10 show that the composition has a biocidal activity against Gram negative bacteria in young chicks (1–14 days old) and chicken (45 days old) based on concentration and exposure time.

TABLE V

Relationship of Composition Concentration to Presence of Salmonella-Negative Broiler Ceca

| Concentration (mM) | % Negative Ceca |
|---|---|
| 0 | 47.5 |
| 1 | 70 |
| 1.33 | 93.3 |
| 2 | 90.0 |
| 4 | 70.0 |

EXAMPLE 11

This study was conducted to evaluate the therapeutic, production and immunostimulatory effect of the composition under market conditions in broilers infected with the gumboro virus.

Gumboro is a reo-like virus that causes an infectious bursal disease, commonly referred to as gumboro disease. The virus is prevalent in most of the concentrated poultry producing areas of the world and may account for considerable losses in individual flocks. Losses result from the clinical disease or from immunosuppression as a result of early infections with the virus. Sequelae that have been associated with immunosuppression induced by the virus include gangrenous dermatitis, inclusion body hepatitis-anemia syndrome, and vaccination failures. It is now considered that the greatest economic loss results from immunosuppressive infections rather than from the clinical disease produced by the virus.

In this study, 1 mM of the composition was administered to the broilers' drinking water for 25 days. At day 14 all the chickens received a vaccine. All the broilers had unlimited access to the water throughout the entire study. The effect of the composition on the mortality was recorded daily, and body weight gain was monitored at 35 and 42 days.

The broilers that received the composition had a 15.3% lower mortality rate than the control group after 25 days. At market age (42 days), the mortality was reduced by 29.7%. The birds that received the composition had, on average, 5.35% greater body weight after 35 days and 2.03% greater body weight after 42 days compared to the control group.

This study demonstrates that the composition has a therapeutic, production, and immunostimulatory effect in broilers raised under market conditions. Additionally, the study demonstrates that the administration of the compound in the drinking water of infected broilers ameliorates the negative effects associated with infectious bursal disease. The results of the study further indicate that administration of the composition is a superior alternative to the less effective vaccination route of treatment.

EXAMPLE 12

This study was conducted to evaluate the therapeutic and production activity of the composition on turkey poults infected with *Bordetella avium*. *B. avium* is the causative organism of turkey coryza, a poultry disease that has no effective vaccine and limited avenues for treatment. In this study, the composition was diluted to final concentrations of 1 mM and 2 mM in the turkey poults' drinking water. All the turkeys had unlimited access to the water throughout the 17 days of the study.

The data presented in Table VI demonstrate the influence of the composition on poult body weight. At hatching, no statistical differences in body weights were noted among treatment groups. At 7 days of age, 6 days post-inoculation with *B. avium,* infected poults receiving only tap water exhibited a marked suppression in body weight when compared to all other treatment groups. Infected poults receiving 1 mM or 2 mM of the composition displayed numerically larger 7-day body weights than either infected poults receiving tap water or noninfected poults provided with tap water. The *B. avium*-associated suppression in growth was also evident at 14 and 17 days. At these ages, the administration of the composition mitigated the growth suppressive effects of the *B. avium* infection.

TABLE VI

Influence of Administration of the Composition on Body Weights (g) of *B.-avium*-Infected Poults

| Composition Concentration | Age | | | |
|---|---|---|---|---|
| (mM) | hatch | 7 days | 14 days | 17 days |
| non-infected | | | | |
| 0 | 61.9 | 137.4 | 318.2 | 437.1 |
| 1 | 62.9 | 134.2 | 309.8 | 424.7 |
| 2 | 61.8 | 141.8 | 324.8 | 436.5 |
| infected | | | | |
| 0 | 62.9 | 117.9 | 262.8 | 336.9 |
| 1 | 62.8 | 137.6 | 330.2 | 436.3 |
| 2 | 61.7 | 141.5 | 333.5 | 445.4 |

Feed conversion ratios (FCR) and feed consumption data are depicted in Table VII. Significantly greater amounts of the starter diet were required to produce a unit gain in body weight for those poults inoculated with *B. avium* and placed on tap water from hatching to 7 days of age. Again the presence of the composition eliminated this effect associated with *B. avium.* A marked decline in feed intake occurred in infected poults receiving tap water during the 7- to 14-day period.

TABLE VII

Influence of Administration of the Composition on FCR and Feed Consumption of *B.-avium*-Infected Poults

| Composition Concentration | FCR (g feed/g gain) | | consumption (g) | |
|---|---|---|---|---|
| (mM) | 0–7 days | 7–14 days | 0–7 days | 7–14 days |
| non-infected | | | | |
| 0 | 1.201 | 1.296 | 87.5 | 234.3 |
| 1 | 1.204 | 1.278 | 85.4 | 232.5 |
| 2 | 1.150 | 1.304 | 91.9 | 237.5 |
| infected | | | | |
| 0 | 1.443 | 1.325 | 77.6 | 191.7 |
| 1 | 1.196 | 1.247 | 89.4 | 234.0 |
| 2 | 1.172 | 1.203 | 93.5 | 227.7 |

Significant reductions in rates of weight gain were also noted in infected poults receiving tap water from 0–7 and 7–14 days of age compared to weight gain for infected poults receiving drinking water fortified with the composition (Table VIII).

The data showed that the administration of the composition in the drinking water of turkeys eliminated the decline in feed efficiency associated with the *B. avium* infection.

TABLE VIII

Influence of Administration of the Composition on the Rate of Weight Gain of *B.-avium*-Infected Poults

| Composition Concentration | gain (g) | |
|---|---|---|
| (mM) | 0–7 days | 7–14 days |
| non-infected | | |
| 0 | 73.2 | 181.0 |

TABLE VIII-continued

Influence of Administration of the Composition
on the Rate of Weight Gain of *B.-avium*-Infected Poults

| Composition Concentration | gain (g) | |
|---|---|---|
| (mM) | 0–7 days | 7–14 days |
| 1 | 71.3 | 182.0 |
| 2 | 79.9 | 182.5 |
| infected | | |
| 0 | 55.0 | 145.0 |
| 1 | 74.8 | 188.0 |
| 2 | 79.9 | 192.0 |

Electron microscopy showed that damage to the tracheal epithelium in infected poults was reduced by the supplementation of the composition. *B. avium* was re-isolated by colony morphology on nutrient agar supplemented with streptomycin (200 µg/mL) and on MacConkey Agar. Based on *B. avium* isolation, no clear differences in treatment trends were observed between infected poults receiving tap water and those receiving the composition.

These findings are of potential significance for a number of reasons. First, turkey coryza or bordetellosis affects upwards of 50% of turkey flocks of several U.S. states in the summer. It is also a highly contagious disease, whose causative organism can survive for months in the turkey house environment. Secondly, a number of avian veterinarians have indicated that the vaccine available for coryza is both expensive and of limited effectiveness. Finally, antibiotics provide very limited improvements in clinical symptoms. This may be due to the fact that getting adequate levels of antibiotic to the primary site of infection (upper respiratory tract) is unlikely. Data from this study showed that the administration of the composition mitigates many of the detrimental effects associated with a *B. avium* infection. This assessment is supported by gross changes in growth, feed utilization, appetite, and structural integrity of the trachea.

These data also suggest that the mitigating effects of the composition are not achieved through elimination of the organism. This observation suggests that the composition has a stimulatory effect on the immune system.

EXAMPLE 13

This study was conducted to evaluate the therapeutic activity of the composition on mortality rates among turkeys infected with rotavirus, reovirus and coronavirus, all of which are believed to be components of what is known as the spiking mortality disease. It has been found that "spiking mortality" is mainly considered a mild disease syndrome but results in major economic loss. Spiking mortality is defined as a phenomenon in which birds exhibit a clinical presentation initially indistinguishable from that of poultry enteritis complex; however, instead of responding to treatment or management manipulation, birds quickly worsen and mortality increases exponentially to exceed 1% mortality for three successive days and in many cases may exceed 3% mortality/day. This is a devastating disease syndrome which results in mortality losses greater than 30% and in some instances has resulted in destruction of the entire flock in the brooder house.

In this study, 2 mM of the composition was administered to newborn turkeys' drinking water for the first 21 days of their lives. All the poults had unlimited access to the water throughout the entire 21 days. The effect of the composition was evaluated every 7 days until the completion of the trial.

The birds infected with the viruses showed 27.1% deaths by day 21. In sharp contrast, the turkeys infected with the viruses and receiving the composition had only 6.3% deaths by day 21. The administration of the composition was found to be beneficial even in uninfected poults. By day 21 noninfected birds had a 4.9% mortality rate, while noninfected birds treated as above with the composition had a mortality rate of only 2.6%.

EXAMPLE 14

This study was conducted to investigate the effect of the composition on feed utilization under market conditions with healthy swine. The composition was administered in the pigs' drinking water in two separate trials, using final concentrations of 1 mM and 2 mM, respectively. The pigs had unlimited access to the water throughout the trials. Food intake per kilogram of weight gain was compared at the end of 21 days in both of the trials.

Tables IX and X show the improved feed utilization in the pigs that had consumed the water treated with the composition following the two respective 21-day trials. Feed intake per kilogram of weight gain was 7.0% and 7.4% lower in the trial group than in the control group for trials 1 and 2, respectively. Feed intake per pig per day was 6.3% and 7.9% lower in the trial group than in the control group for trials 1 and 2, respectively.

This study demonstrated that feed utilization is improved when different concentrations of the composition are administered in the drinking water of healthy swine under market conditions.

TABLE IX

Influence of Administration of the Composition (1 mM)
on FCR and Feed Consumption of Healthy Swine

| | CONTROL GROUP | TRIAL GROUP | DIFF. % |
|---|---|---|---|
| Number of pigs: | 22 | 23 | +4.5% |
| Average weight start: | 31.4 kg | 30.8 kg | −1.9% |
| Average weight end: | 46.4 kg | 45.9 kg | −1.1% |
| Total weight gain: | 330.0 kg | 347.3 kg | +5.0% |
| Weight gain/day/pig: | 714 g | 719 g | +0.7% |
| Feed intake total: | 662 FU* | 650 FU | −1.8% |
| Feed intake/pig/day: | 1.43 FU | 1.34 FU | −6.3% |
| Feed intake/kg weight gain: | 2.01 FU | 1.87 FU | −7.0% |

*Feed unit = 0.95 kg feed

TABLE X

Influence of Administration of the Composition (2 mM)
on FCR and Feed Consumption of Healthy Swine

| | CONTROL GROUP | TRIAL GROUP | DIFF. % |
|---|---|---|---|
| Number of pigs: | 12 | 15 | +25.0% |
| Average weight start: | 34.1 kg | 30.6 kg | −10.3% |
| Average weight end: | 48.8 kg | 45.2 kg | −7.4% |
| Total weight gain: | 177.0 kg | 219.0 kg | +23.7% |
| Weight gain/day/pig: | 702 g | 695 g | −1.0% |

TABLE X-continued

Influence of Administration of the Composition (2 mM) on FCR and Feed Consumption of Healthy Swine

|  | CONTROL GROUP | TRIAL GROUP | DIFF. % |
|---|---|---|---|
| Total feed intake: | 383.3 FU | 442.1 FU | +15.3% |
| Feed intake/pig/day: | 1.52 FU | 1.40 FU | −7.9% |
| Feed intake/kg weight gain: | 2.17 FU | 2.01 FU | −7.4% |

EXAMPLE 15

This commercial study was conducted to evaluate the effect of the administration of the composition on weight gain and mortality rate of healthy broilers under market conditions.

In this study the composition at 2 mM was administered in the broilers' drinking water. All the broilers had unlimited access to the water throughout the entire 37 days of the study. The effect of the composition on weight gain and mortality rate was evaluated every 7 days until the completion of the trial.

Improved weight gain and a lower mortality rate were observed in the broilers that had consumed the water treated with the composition during the 37-day trial. Weight gain was improved by 2.22% in the trial group compared to the control group after 36 days. The broilers that were in the trial group had a 0.57% lower mortality rate than the control group after 37 days.

This study demonstrates that rate of body weight gain increases and mortality rate decreases when the compound is administered in the drinking water of healthy broilers under market conditions.

We claim:

1. A therapeutic and production method for decreasing the dependence on vaccines and antibiotics and stimulating the immune system of healthy or infected food animals, which comprises orally administering to the animals an effective amount of a pH-buffered, redox-stabilized composition comprising halide and oxyhalide ions and wherein the pH of the composition is in the range from 7.5 to 13.

2. A therapeutic and production method for decreasing the dependence on vaccines and antibiotics and stimulating the immune system of healthy or infected food animals, which comprises orally administering to the animal an effective amount of a pH-buffered, redox-stabilized composition comprising a chlorite ion source, a chloride ion source and a chlorate ion source wherein the molar ratio of chlorite ion to chlorate ion is in the range from 2:1 to 1000:1; the molar ratio of chlorite ion to chloride ion is in the range from 0.1:1 to 1000:1; and the molar ratio of chloride ion to chlorate ion is in the range from 0.1:1 to 1000:1.

3. The method of claim 2 wherein the molar ratio of chlorite ion to chlorate ion is in the range from 3:1 to 500:1; and the molar ratio of chlorite ion to chloride ion is in the range from 1:1 to 50:1.

4. The method of claim 2 wherein the molar ratio of chlorite ion to chlorate ion is in the range from 3:1 to 16:1; the molar ratio of chlorite ion to chloride ion is in the range from 0.8:1 to 5:1; and the molar ration of chloride ion to chlorate ion is in the range from 4:1 to 16:1.

5. The method of claim 4 wherein the molar ratio of chlorite ion to chlorate ion is 11.8:1; the molar ratio of chlorite ion to chloride ion is 1.12:1; and the molar ratio of chloride ion to chlorate ion is 10.5:1.

6. The method of any one of claims 2–5 wherein the chlorite ions are present in the concentration range from 0.01 mM to 1.0 M.

7. The method of claim 1 wherein the composition comprises bromide and oxybromide ions.

8. The method of any one of claims 2–5 wherein the pH of the composition is in the range from 7.5 to 13.

* * * * *